United States Patent
Govari et al.

(10) Patent No.: US 10,610,610 B2
(45) Date of Patent: Apr. 7, 2020

(54) HYDROGEN PEROXIDE STERILIZER WITH MULTIPLE UV SENSORS

(71) Applicant: Biosense Webster (Israel) Ltd., Yokneam (IL)

(72) Inventors: Assaf Govari, Haifa (IL); Andres Claudio Altmann, Haifa (IL); Vadim Gliner, Haifa (IL); Yaron Ephrath, Karkur (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 335 days.

(21) Appl. No.: 15/399,671

(22) Filed: Jan. 5, 2017

(65) Prior Publication Data
US 2018/0185532 A1    Jul. 5, 2018

(51) Int. Cl.
*A61L 2/24* (2006.01)
*A61L 2/20* (2006.01)
*A61L 2/16* (2006.01)

(52) U.S. Cl.
CPC ............ *A61L 2/24* (2013.01); *A61L 2/16* (2013.01); *A61L 2/208* (2013.01); *A61L 2202/122* (2013.01); *A61L 2202/14* (2013.01)

(58) Field of Classification Search
CPC ......... A61L 2/24; A61L 2/208; A61L 2202/14
See application file for complete search history.

(56) References Cited

U.S. PATENT DOCUMENTS

| | | | |
|---|---|---|---|
| 6,269,680 B1 | 8/2001 | Prieve et al. | |
| 6,656,424 B1 | 12/2003 | Deal | |
| 7,880,887 B2 | 2/2011 | Olson et al. | |
| 2003/0156977 A1 | 8/2003 | Kohler et al. | |
| 2004/0013777 A1* | 1/2004 | Hallstadius | A61L 2/208 426/320 |
| 2006/0222576 A1 | 10/2006 | Rudkowski et al. | |
| 2014/0044590 A1 | 2/2014 | Trapani | |
| 2014/0299793 A1* | 10/2014 | Deng | A61L 2/10 250/504 R |

FOREIGN PATENT DOCUMENTS

| | | |
|---|---|---|
| EP | 2000156 A2 | 12/2008 |
| EP | 2337588 B1 | 3/2016 |
| WO | WO 2003/006963 A1 | 1/2003 |
| WO | WO 2013/143859 A1 | 10/2013 |

OTHER PUBLICATIONS

European Search Report and Written Opinion dated May 4, 2018 for Application No. 18150366.5, 6 pages.

* cited by examiner

*Primary Examiner* — Kevin Joyner
(74) *Attorney, Agent, or Firm* — Frost Brown Todd LLC

(57) ABSTRACT

Sterilization is carried out by admitting a flow of sterilant fluid into a sterilization chamber through an inlet, emitting ultraviolet light into the chamber, receiving the ultraviolet light in a plurality of ultraviolet light detectors disposed at respective locations; and regulating the flow of the sterilant fluid responsively to signals from the detectors to achieve a desired level of the sterilant fluid in the chamber.

19 Claims, 3 Drawing Sheets

HYDROGEN PEROXIDE STERILIZER WITH MULTIPLE UV SENSORS

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to systems that analyze fluids by determining their chemical or physical properties. More particularly, this invention relates to determining the concentration of a gas in a sterilization chamber.

2. Description of the Related Art

One of the standard methods for low temperature sterilization of medical equipment is to use a combination of hydrogen peroxide (hydrogen peroxide) vapor with a low temperature plasma in a sterilization chamber. During the course of the sterilization process the hydrogen peroxide concentration is measured as it is consumed, and as necessary hydrogen peroxide is added to the chamber to maintain the concentration at a satisfactory level. A present method for measuring the hydrogen peroxide concentration uses an ultraviolet light source transmitting through the chamber, and the received ultraviolet light is measured with a single ultraviolet light detector that is located far from the source. The level of the received ultraviolet light is used to calculate a gross hydrogen peroxide concentration reading.

One arrangement for measuring concentration of a sterilant is proposed in U.S. Pat. No. 7,880,887 to Olson et al. Measurements of the concentration of the sterilant in a sterilization chamber are provided through the use of a light source, a first detector that receives light from the light source that has not passed through the sterilization chamber and a detector that receives light from the light source that has passed through the sterilization chamber. The light contains wavelengths known to be absorbed by the sterilant. A controller receives and processes signals received from the two detectors to cancel changes in the output of the light source and then apply a modified Beer-Lambert law to determine the concentration of the sterilant gas.

In practice, concentration of a sterilant such as hydrogen peroxide may vary within the chamber, especially when sterilizing equipment with narrow lumens, such as catheters restricts diffusion of sterilant vapor. There may be areas of the chamber, which are exposed to higher or lower concentrations of hydrogen peroxide due to such flow restrictions. Thus the gross reading referred to above may not give an accurate picture of the concentration distribution over the chamber.

The art has recognized that measurements in different areas of the sterilization chamber may improve the reliability of the readings of sterilant gas concentration. For example, U.S. Pat. No. 6,269,680 to Prieve et al. proposes includes a movable gas cell, which can be moved around the sterilization chamber so that measurements of the concentration of hydrogen peroxide can be done at various locations inside the sterilization chamber. The ends of the movable gas cell are connected to an ultraviolet lamp and a detector with optical fibers.

SUMMARY OF THE INVENTION

Embodiments of the invention use multiple ultraviolet (UV) detectors distributed over a sterilization chamber. The detectors may be relatively small (of the size of a coin), and may be configured to transmit their readings wirelessly to a central processor. In addition, rather than a single UV source, a double wavelength source is used to exploit differential absorption. To further improve the accuracy of the concentration readings, the source may be pulsed, which improves the signal-to-noise ratio.

There is provided according to embodiments of the invention a sterilization chamber having an inlet for admitting a flow of sterilant fluid into the chamber, an ultraviolet light emitter arranged to direct ultraviolet light into the chamber, a plurality of ultraviolet light detectors disposed at respective locations for receiving the ultraviolet light, and a controller for regulating the flow of the sterilant fluid responsively to signals from the detectors to achieve a desired level of the sterilant fluid in the chamber.

According to one aspect of the apparatus, the emitter emits light at a first wavelength that is absorbed by the sterilant fluid and at a second wavelength that is less well absorbed by the sterilant fluid.

According to a further aspect of the apparatus, the sterilant fluid is hydrogen peroxide, the first wavelength is 280 nm and the second wavelength is 370 nm.

According to yet another aspect of the apparatus, the emitter includes a plurality of emitters having optics arranged to direct light emissions to respective detectors.

According to still another aspect of the apparatus, the chamber is maintained at lower than atmospheric pressure.

According to an additional aspect of the apparatus, the emitter includes a plurality of light emitting diodes that are configured to emit at respective frequencies.

According to another aspect of the apparatus, the emitter includes a plurality of light emitting diodes that are configured to emit at identical frequencies at different time intervals.

There is further provided according to embodiments of the invention a method, which is carried out by admitting a flow of sterilant fluid into a sterilization chamber through an inlet, emitting ultraviolet light into the chamber, receiving the ultraviolet light in a plurality of ultraviolet light detectors disposed at respective locations, and regulating the flow of the sterilant fluid responsively to signals from the detectors to achieve a desired level of the sterilant fluid in the chamber.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 1:
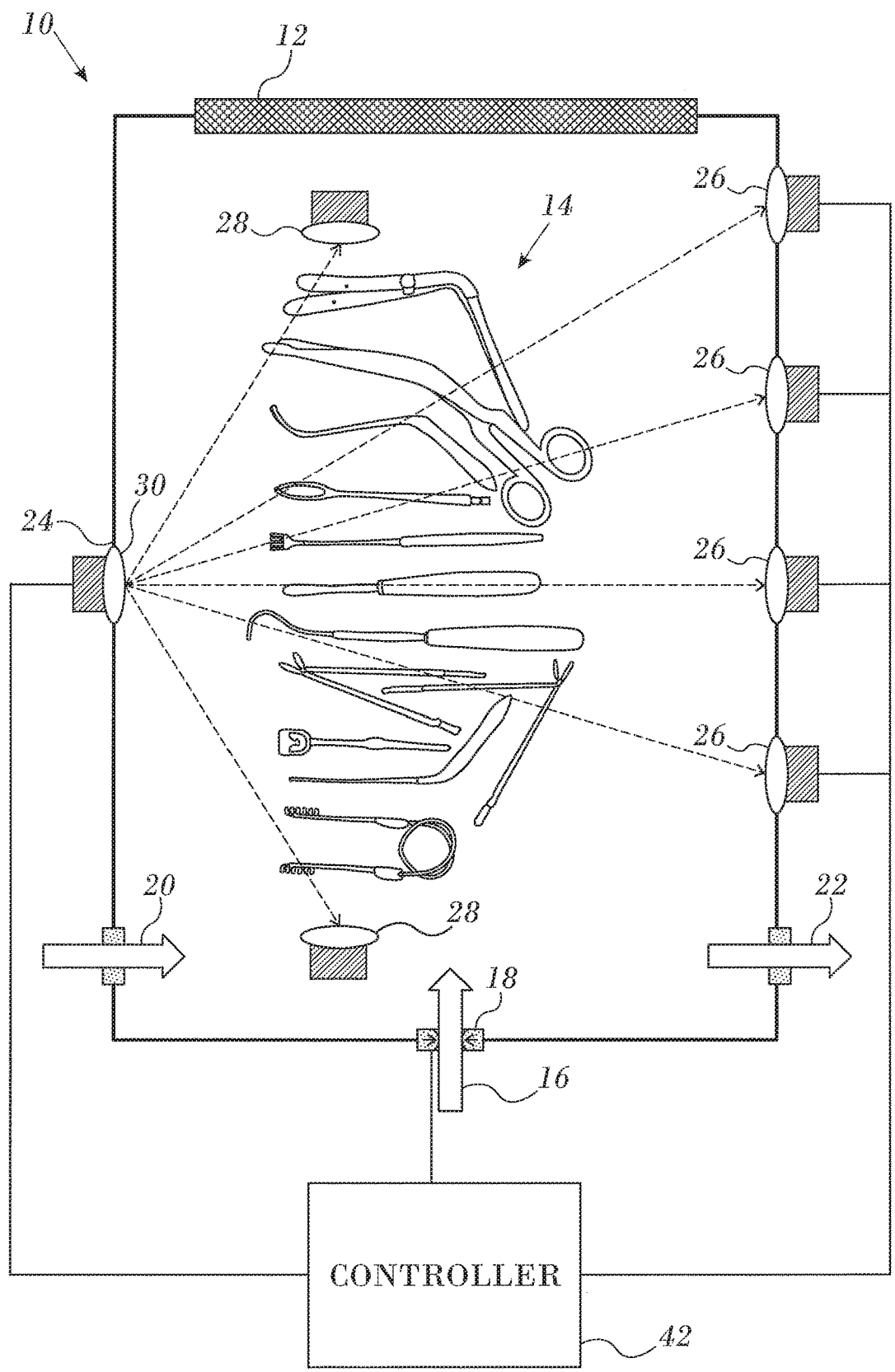
FIG. 1 is a schematic diagram of a sterilization chamber in accordance with an embodiment of the invention.

Turning now to the drawings, Reference is made to FIG. 1, which is a schematic diagram of a sterilization chamber 10 in accordance with an embodiment of the invention. The chamber 10 has a sealed portal 12 for passage of objects 14, which can be assorted surgical instruments and the like. Hydrogen peroxide is admitted into the chamber 10 via an inlet 16 having a regulator or valve 18. A portal 20 is provided for admission of air, and gas exits from the chamber through a portal 22. The chamber 10 is maintained at lower than atmospheric pressure, typically 0.5 torr, and features an ultraviolet light source 24 that transmits ultraviolet light through the chamber, which is received in multiple mural ultraviolet light detectors 26 and interior ultraviolet light detectors 28. Optics 30 having appropriate UV (ultraviolet) lenses that are associated with the ultraviolet source 24 are configured to illuminate all the detectors 26, 28. The distribution of the detectors 26, 28 in FIG. 1 is by way of example and not of limitation. The detectors 26, 28 may be distributed in the chamber such that the measurements optimally reflect the concentrations of hydrogen peroxide at the objects being sterilized. The detectors need not be distributed in any particular order, and may even be widely scattered about and within the chamber, facing in different directions.

The ultraviolet source 24 receives command signals from a controller 42 and readouts from the detectors 26, 28. The valve 18 is adjusted by the controller 42 responsively to the readouts. The valve 18 regulates the inflow of hydrogen peroxide so as to achieve a desired optimum level (typically 95% concentration) of hydrogen peroxide within the chamber 10. Once the optimum level is achieved, in some embodiments the inflow may be discontinued and the chamber maintained in a static condition.

Figure 2:
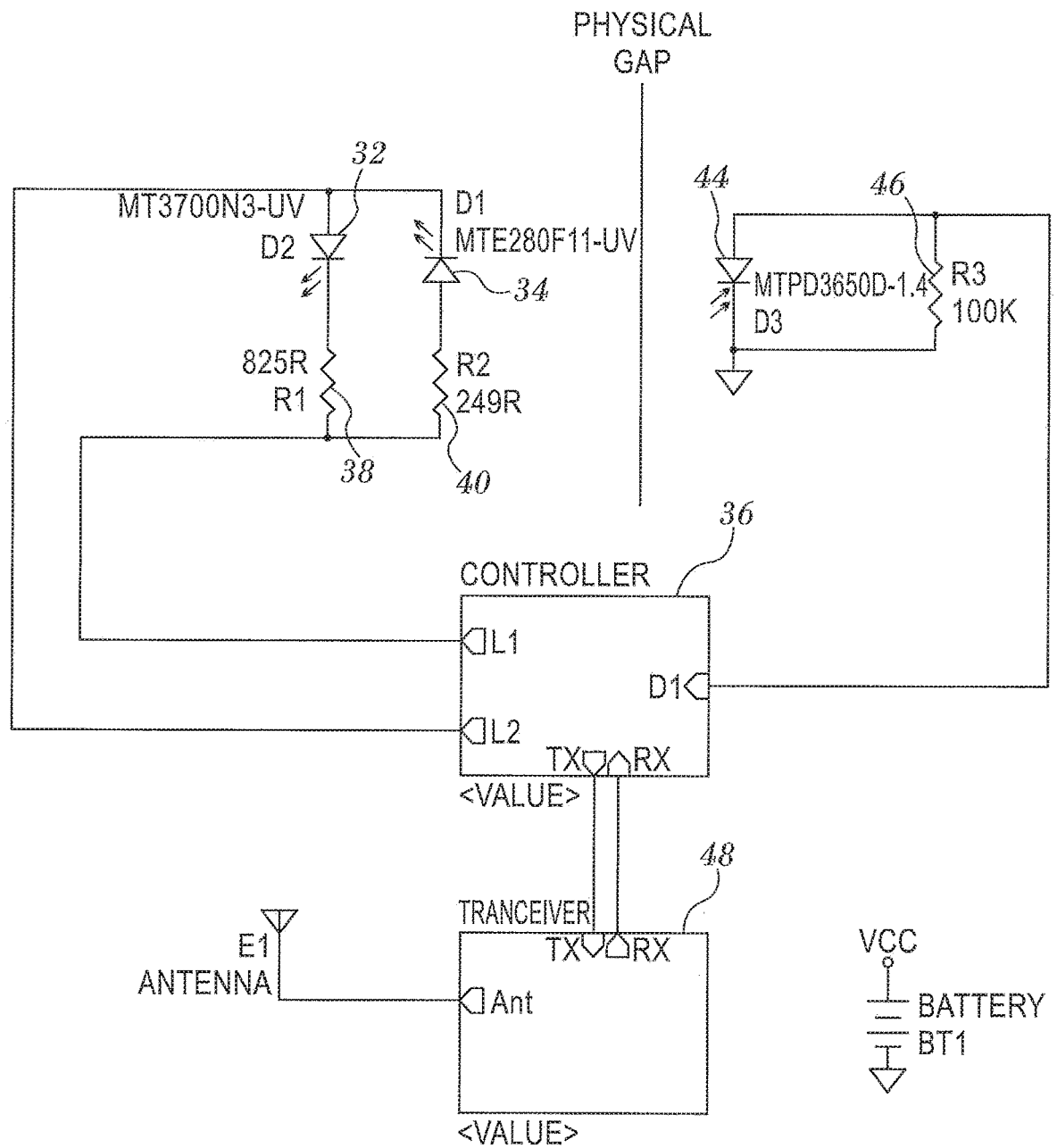
FIG. 2 is an electrical schematic of components of the chamber shown in FIG. 1 in accordance with an embodiment of the invention.

Continued reference is made to FIG. 1 and also to FIG. 2, which is an electrical schematic of components of the chamber 10 in accordance with an embodiment of the invention. Ultraviolet source 24 is realized as two light emitting diodes 32, 34 in parallel, both supplied by a controller 36. The diodes 32, 34 are in series with resistors 38, 40 and emit at 280 nm and 370 nm respectively. The diodes may emit simultaneously at respective frequencies, or at different time intervals at the same frequency. The Goertzel algorithm may be used in detecting the signals from the diodes 32, 34. Techniques of dual wavelength ultraviolet spectroscopy are known, for example, from U.S. Pat. No. 6,269,680, which is herein incorporated by reference. In the circuitry shown in FIG. 2 diode 34 acts as a reference to compensate for internal variations in the circuitry, while diode 32 emits at a wavelength that is strongly absorbed by hydrogen peroxide vapor.

A number of other ultraviolet emitters known in the art could be used for the ultraviolet source 24, for example, cylindrical low pressure mercury UV emitters with a spectral peak at about 254 nm. Such emitters are proposed in U.S. Patent Application Publication No. 2006/0222576, issued as U.S. Pat. No. 7,696,490 on April 13, 2010, which is herein incorporated by reference. Other examples of such light sources include low pressure mercury vapor lamps, deuterium lamps, xenon lamps, light-emitting diodes and laser diodes. In general all of these are less convenient or more expensive than the dual light emitting diode configuration described above.

The detectors 26, 28 are realized as a charge-coupled detector 44 across a resistor 46. Signals from the detector 44 are received in the controller 36 and conveyed to a remote site, such as a processor (not shown) by transceiver 48, where signal processing techniques are applied, including analog-to-digital conversion, and Fourier analysis, including the above-noted Goertzel algorithm.

First Alternate Embodiment

Figure 3:
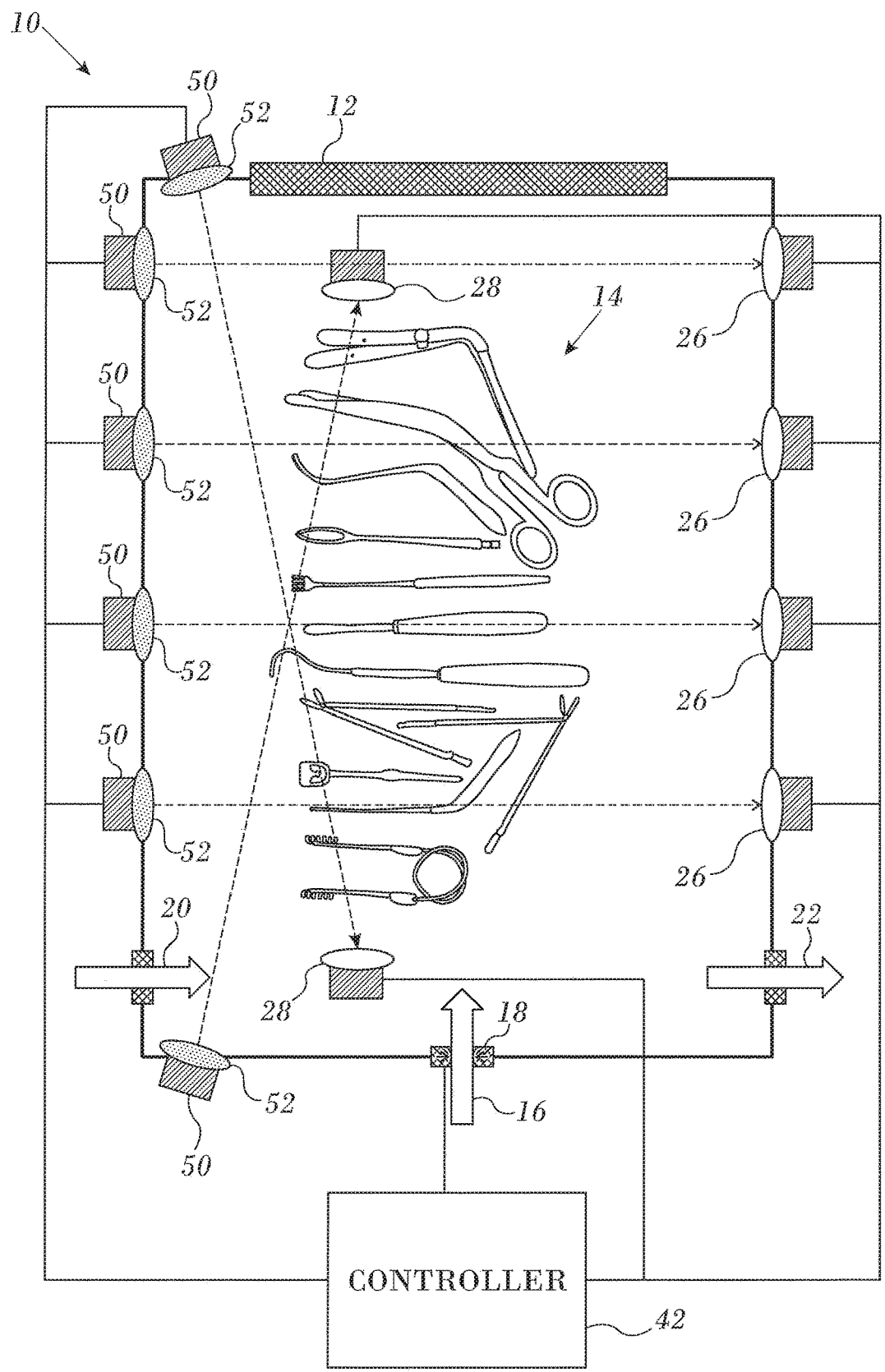
FIG. 3 is a schematic diagram of a sterilization chamber in accordance with an alternate embodiment of the invention.

Reference is now made to FIG. 3, which is a schematic diagram of a sterilization chamber 10 in accordance with an alternate embodiment of the invention in accordance with an embodiment of the invention. In this embodiment there are multiple ultraviolet sources 50, having optics 52 that direct the ultraviolet light toward respective detectors 26, 28. The optics of the detectors 26, 28 may include a convex lens. The light paths between the sources 50 and the detectors 26, 28 are indicated by broken lines.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus, comprising:
   (a) a sterilization chamber having an inlet for admitting a flow of hydrogen peroxide into the chamber;
   (b) an ultraviolet light emitter arranged to direct ultraviolet light into the chamber;
   (c) a plurality of ultraviolet light detectors disposed at respective locations and configured to receive the ultraviolet light; and
   (d) a controller configured to regulate the flow of the sterilant fluid responsively to signals from the detectors to achieve a desired level of the sterilant fluid in the chamber;
   wherein the ultraviolet light emitter is configured to emit light at a first wavelength of 280 nm that is absorbed by the hydrogen peroxide and at a second wavelength of 370 nm that is less well absorbed by the hydrogen peroxide and wherein the chamber is configured to be maintained at lower than atmospheric pressure.

2. The apparatus according to claim 1, wherein the emitter comprises a plurality of emitters having optics arranged to direct light emissions to respective detectors.

3. The apparatus according to claim 1, wherein the emitter comprises a plurality of light emitting diodes that are configured to emit at respective frequencies.

4. The apparatus according to claim 1, wherein the emitter comprises a plurality of light emitting diodes that are configured to emit at identical frequencies at different time intervals.

5. An apparatus, comprising:
(a) a sterilization chamber having an inlet for admitting a flow of sterilant fluid into the sterilization chamber;
(b) an ultraviolet light emitter arranged to direct ultraviolet light into the chamber, wherein the ultraviolet light emitter comprises a plurality of ultraviolet light emitting diodes that are configured to emit ultraviolet light at different time intervals;
(c) a plurality of ultraviolet light detectors that are:
(i) disposed at different locations in the chamber, and
(ii) configured to receive ultraviolet light; and
(d) a controller configured to regulate the flow of the sterilant fluid in response to signals from the ultraviolet light detectors to achieve a desired level of the sterilant fluid in the sterilization chamber,
wherein an object to be sterilized is located within the sterilization chamber.

6. The apparatus according to claim 5, wherein each of the plurality of ultraviolet light emitting diodes is configured to direct ultraviolet light to a single one of the plurality of ultraviolet light detectors.

7. The apparatus according to claim 5, wherein the plurality of light emitting diodes are configured to emit ultraviolet light at the same frequency.

8. The apparatus according to claim 5, wherein the plurality of light emitting diodes are configured to emit ultraviolet light at different frequencies.

9. The apparatus according to claim 5, wherein the sterilization chamber comprises:
(i) a first inner side wall, and
(ii) a second inner side wall disposed opposite to the first inner side wall;
and further wherein:
(i) the ultraviolet light emitter is disposed proximate to the first inner side wall, and
(ii) a first portion of the plurality of ultraviolet light detectors is disposed proximate to the second inner side wall.

10. The apparatus according to claim 9, wherein a second portion of the ultraviolet light detectors is disposed between the first inner side wall and the second inner side wall.

11. The apparatus according to claim 5, wherein the apparatus is configured to sterilize medical equipment disposed inside the sterilization chamber between the first inner side wall and the second inner side wall.

12. The apparatus according to claim 5, wherein the emitter is configured to emit light at a first wavelength of 280 nm that is absorbed by the sterilant fluid and at a second wavelength of 370 nm that is less well absorbed by the sterilant fluid.

13. The apparatus according to claim 12, wherein the sterilant is hydrogen peroxide.

14. An apparatus comprising a sterilization chamber, wherein the sterilization chamber comprises:
(a) a first inner sidewall;
(b) a second inner sidewall disposed opposite to the first inner side wall;
(c) an inlet for admitting a flow of a sterilant into the sterilization chamber;
(d) a plurality of ultraviolet light emitters disposed in discrete locations proximate to the first inner sidewall, wherein the plurality of ultraviolet light emitters is connected to the first inner sidewall;
(e) a plurality of ultraviolet light detectors, wherein a first portion of the plurality of ultraviolet light detectors is disposed in discrete locations proximate to the second inner sidewall, wherein the plurality of ultraviolet light detectors is connected to the second inner sidewall; and
(d) a controller configured to regulate the flow of the sterilant fluid in response to signals from the plurality of ultraviolet light detectors to achieve a desired level of the sterilant fluid in the sterilization chamber;
wherein each of the plurality of ultraviolet light emitters is configured to direct ultraviolet light to a single ultraviolet light detector among the plurality of ultraviolet light detectors.

15. The apparatus according to claim 14, wherein a second portion of the ultraviolet light detectors is disposed between the first inner side wall and the second inner side wall.

16. The apparatus according to claim 14, wherein the apparatus is configured to sterilize medical equipment disposed inside the sterilization chamber between the first inner side wall and the second inner side wall.

17. The apparatus according to claim 14, wherein:
(a) a first portion of the plurality of the ultraviolet light emitters are configured to emit light at a first wavelength of 280 nm, and
(b) a second portion of the plurality of ultraviolet light emitters are configured to emit light at a second wavelength of 370 nm.

18. The apparatus according to claim 17, wherein the sterilant is hydrogen peroxide.

19. The apparatus according to claim 14, wherein the plurality of ultraviolet light emitters are configured to emit ultraviolet light at different frequencies.

* * * * *